(12) United States Patent  
Clement et al.

(10) Patent No.: US 8,308,772 B2
(45) Date of Patent: Nov. 13, 2012

(54) VERTEBRAL OSTEOSYNTHESIS EQUIPMENT

(75) Inventors: Jean-Luc Clement, La Colle sur Loup (FR); Vincent Fiere, Collonge au Mont d'Or (FR); Jean Taylor, Cannes (FR); Yves Adam, Authie (FR); Bernard Villaret, Croix-Chapeau (FR)

(73) Assignee: Medicrea Technologies, La Rochelle (FR)

( * ) Notice: Subject to any disclaimer, the term of this patent is extended or adjusted under 35 U.S.C. 154(b) by 62 days.

(21) Appl. No.: 12/954,718

(22) Filed: Nov. 26, 2010

(65) Prior Publication Data

US 2011/0112580 A1    May 12, 2011

Related U.S. Application Data

(63) Continuation-in-part of application No. 10/561,915, filed as application No. PCT/IB2004/002395 on Jun. 24, 2004, now Pat. No. 7,862,593.

(60) Provisional application No. 60/490,516, filed on Jul. 29, 2003.

(30) Foreign Application Priority Data

Jun. 27, 2003   (FR) ...................................... 03 07779

(51) Int. Cl.
*A61B 17/70* (2006.01)
(52) U.S. Cl. .................... 606/267; 606/277; 606/916
(58) Field of Classification Search .......... 606/250–278, 606/86 A, 914–916; 81/125, 451, 452, 454; 403/109.2; 411/386
See application file for complete search history.

(56) References Cited

U.S. PATENT DOCUMENTS

| | | | |
|---|---|---|---|
| 809,880 A | 1/1906 | Wooldridge et al. | |
| 903,904 A | 11/1908 | Smith | |
| 1,454,789 A | 5/1923 | Rentchler | |
| 2,320,967 A * | 6/1943 | Dunkelberger | 294/100 |
| 2,372,930 A | 11/1943 | Bovee | |
| 2,381,597 A | 8/1945 | Johnson | |
| 2,404,580 A | 7/1946 | Van Schwartz | |
| 2,679,778 A | 6/1954 | Krafft | |
| 3,545,066 A | 12/1970 | Stillman et al. | |
| 4,741,229 A | 5/1988 | Rachanski et al. | |
| 4,940,467 A | 7/1990 | Tronzo | |
| 5,217,462 A | 6/1993 | Asnis et al. | |
| 5,464,407 A | 11/1995 | McGuire | |
| 5,507,817 A | 4/1996 | Craig et al. | |
| 5,588,564 A * | 12/1996 | Hutson et al. | 222/383.1 |

(Continued)

FOREIGN PATENT DOCUMENTS

EP    0 786 235    7/1997

(Continued)

*Primary Examiner* — Jan Christopher Merene

(74) *Attorney, Agent, or Firm* — Young & Thompson

(57) ABSTRACT

Vertebral osteosynthesis equipment includes bony anchoring members, such as pedicular screws or hooks, at least one of which includes a proximal threaded stud for receiving a nut and a base portion for anchoring to a vertebra; linking rods, intended to be connected to these anchoring members and attached to the vertebrae by these anchoring members, parts for connecting these linking rods to the anchoring members, and extension pieces for engaging on the proximal stud(s) of the anchoring member(s) for running down connecting parts on this or these proximal stud(s) until they rest on the proximal zone(s) of the base portion(s) of the anchoring members. The proximal stud of at least one anchoring member and the extension piece intended to be used with this anchoring member include positioning elements for positioning the extension piece on the free end of the proximal stud, concentrically thereto.

7 Claims, 2 Drawing Sheets

U.S. PATENT DOCUMENTS

| | | |
|---|---|---|
| 5,613,968 A | 3/1997 | Lin |
| 5,735,851 A | 4/1998 | Errico et al. |
| 5,814,046 A | 9/1998 | Hopf |
| 6,009,779 A | 1/2000 | Mastroni |
| 6,010,507 A | 1/2000 | Rudloff |
| 6,123,706 A | 9/2000 | Lange |
| 6,267,765 B1 | 7/2001 | Taylor et al. |
| 6,296,656 B1 | 10/2001 | Bolduc et al. |
| 6,482,207 B1 | 11/2002 | Errico |
| 6,543,317 B1 * | 4/2003 | Rinner et al. .................... 81/125 |
| 6,945,980 B2 | 9/2005 | Nguyen et al. |
| 7,163,538 B2 | 1/2007 | Altarac et al. |
| 2002/0095181 A1 | 7/2002 | Beyar |
| 2003/0086772 A1 | 5/2003 | Giannakakos |
| 2004/0064140 A1 | 4/2004 | Taylor et al. |
| 2004/0215190 A1 * | 10/2004 | Nguyen et al. .................. 606/61 |
| 2006/0111718 A1 | 5/2006 | Carli |
| 2006/0149231 A1 | 7/2006 | Bray |
| 2006/0167455 A1 * | 7/2006 | Clement et al. ................. 606/61 |
| 2007/0173817 A1 | 7/2007 | Sournac et al. |
| 2008/0184853 A1 * | 8/2008 | Chen ............................... 81/451 |
| 2008/0195122 A1 | 8/2008 | Castell, VI et al. |
| 2009/0062864 A1 | 3/2009 | Ludwig et al. |

FOREIGN PATENT DOCUMENTS

| | | |
|---|---|---|
| EP | 0 923 908 | 6/1999 |
| WO | WO 94/10928 | 5/1994 |

* cited by examiner

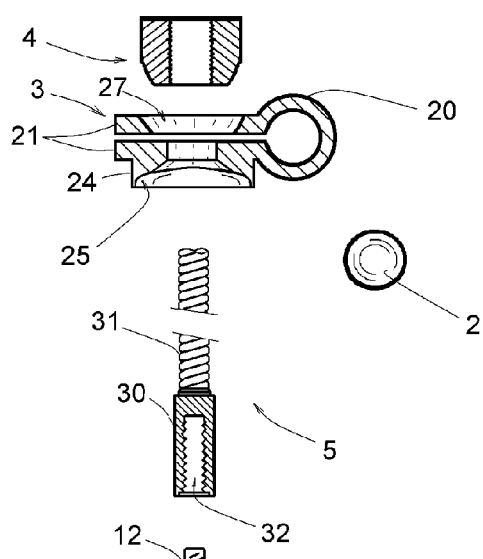
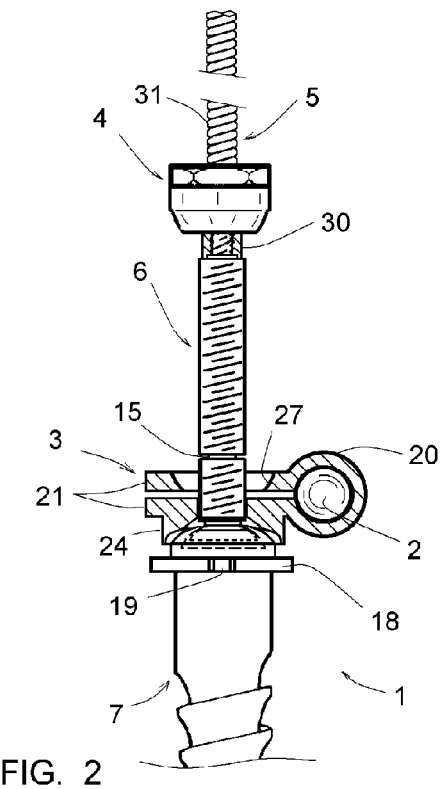
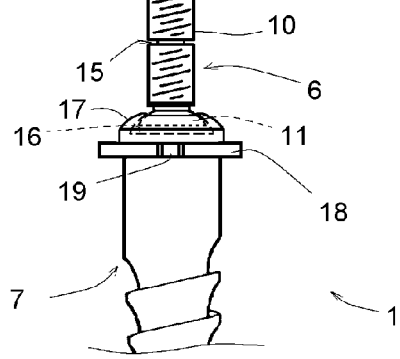
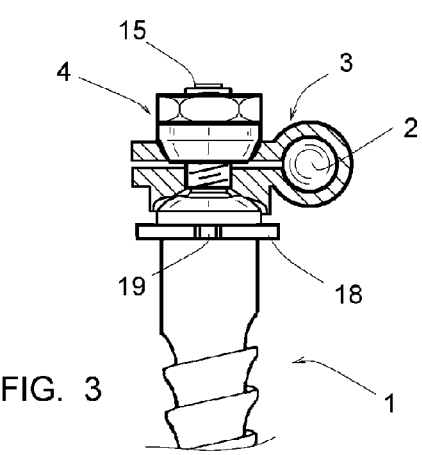
FIG. 1
FIG. 2
FIG. 3

VERTEBRAL OSTEOSYNTHESIS EQUIPMENT

CROSS REFERENCE TO RELATED APPLICATIONS

This application is a new continuation-in-part of application Ser. No. 10/561,915 filed on Apr. 10, 2006, now U.S. Pat. No. 7,862,593, which is the 35 U.S.C. §371 national stage of International PCT/IB04/02395 filed on Jun. 24, 2004, which claims priority to both the U.S. Provisional Application No. 60/490,516, filed on Jul. 29, 2003 and French Application No. 03/07779 filed on Jun. 27, 2003. The entire contents of each of the above-identified applications are hereby incorporated by reference.

FIELD OF THE INVENTION

The present invention relates to vertebral osteosynthesis equipment.

RELATED ART

A vertebral osteosynthesis equipment generally includes bony anchoring members, such as pedicular screws or lamar hooks, one or two linking rods, intended to be connected to these anchoring members and to be attached to the vertebrae by dint thereof, and parts for connecting this(these) linking rod(s) to these anchoring members. The equipment may also comprise length-adjustable crossbeams, which link transversally two parallel linking rods in order to hold said rods with respect to one another.

In an existing type of equipment, each anchoring member comprises a proximal threaded stud and a base portion intended for bony anchoring thereof. Each connecting part comprises a rounded section intended for surrounding a linking rod and two parallel drilled wings, these wings being intended for engaging onto said proximal threaded stud and for being clamped, using a nut screwed on the stud, against a bearing surface provided on said base portion. This clamping causes the clamping of said rounded section around the linking rod and thus ensures longitudinal immobilization of this rod with respect to the anchoring member. The anchoring members may be of "monoaxial" type, i.e. comprise a proximal threaded stud integral with the base portion, or may be of "polyaxial" type, i.e. comprise a proximal threaded stud articulated with respect to that base portion.

When installing the equipment, the anchoring members are placed, then extension pieces are engaged on the proximal studs of these anchoring members. The connecting parts, with the rod(s) engaged in their rounded portions, are then engaged on these extension pieces and run down along the latter until they rest on the proximal zones of the base portions of the anchoring members. The extension pieces are then withdrawn and the clamping nuts are placed.

To enable adequate correction of the position of the vertebrae, the linking rod(s) must be shaped into one or several planes. Such operation leads to successive trials and errors until adequate form is obtained. Successive insertions and retractions of the extension pieces and successive running down operations of the assemblies composed of connecting parts—linking rods along the latter, then withdrawing the extension pieces for placing the nuts, are then relatively tedious and time-consuming operations. Moreover, there is always the risk of nut breaking loose from its installing instrument, and then, the necessity of retrieving this nut before placing it back on said this instrument; all this process contributes to make the implantation of the equipment longer and more complex.

SUMMARY OF THE INVENTION

The purpose of the present invention is to remedy these essential shortcomings, by providing vertebral osteosynthesis equipment which is easier and faster to implant than any extent equipment.

The equipment of the invention includes, in itself,
bony anchoring members, such as pedicular screws or lamar hooks, whereof at least one comprises a proximal threaded stud intended for receiving a nut, and a base portion intended for anchoring to a vertebra;
one or two linking rods, intended to be connected to these anchoring members and to be attached to the vertebrae by dint thereof,
parts for connecting this(these) linking rod(s) to these anchoring members, and
extension pieces intended for engaging on the proximal stud(s) of the anchoring member(s) for running down connecting parts on this or these proximal stud(s) until they rest on the proximal zone(s) of the base portion(s) of the anchoring members.

According to the invention, the proximal stud of at least one anchoring member and the extension piece intended to be used with this anchoring member include positioning means enabling to position the extension piece on the free end of the proximal stud, concentrically thereto, these positioning means being such that the extension piece comprises an end distal portion whereof the external diameter is sized in order to let through the nut thereon.

The extension piece may thus be positioned on the free end of the proximal stud, concentrically thereto, then the nut may be run down towards the implantation site without retracting the extension piece, whereas such descent does induce any risk of losing this nut. There results therefrom that the equipment is placed more quickly and more reliably.

The nut may in particular be engaged on said proximal stud at the same time as the connecting part.

Said positioning means comprise advantageously a rod integral with the proximal stud or of the extension piece and a bore provided, respectively, in the extension piece or the proximal stud, whereas this rod may be engaged in this bore.

Said positioning means comprise advantageously means enabling axial connection of the proximal stud with the extension piece.

The extension piece may therefore no get lost.

According to a preferred embodiment of the invention, the proximal stud comprises a threaded proximal rod, and said end distal portion of the extension piece comprises a tapered hole for screwing the extension piece on this proximal rod.

The extension piece may, outside said end distal portion, be of flexible structure, for easy positioning thereof on the free end of the proximal stud, notably screwing or unscrewing thereof when the threaded rod of the proximal stud is not parallel to the engaging direction of the extension piece.

This flexible structure may notably be in the form of a metal wire wound into a spiral, with preferably contiguous spires. It may also be an elastic wire, a cable or other.

DESCRIPTION OF THE DRAWINGS

The invention will be better understood, and other characteristics and advantages thereof will appear, with reference to the appended schematic drawing, representing, for non-limiting exemplification purposes, preferred embodiments of parts included in the equipment affected.

FIG. 1 is a partial view of a polyaxial pedicular screw, of a linking rod seen from its end, of a connecting part and of a nut, in cross-section, and of an extension piece partially in cross-section, included in a first embodiment of said equipment;

FIG. 2 is a view of these parts similar to FIG. 1, during assembly;

FIG. 3 is a view of these parts similar to FIG. 2, once the assembly completed;

DETAILED DESCRIPTION OF THE INVENTION

Figure 4:
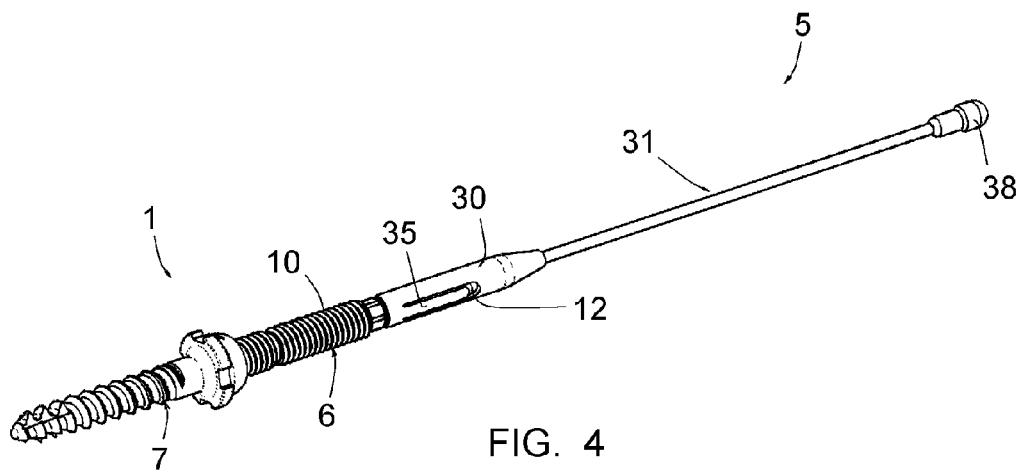
FIG. 4 is a perspective view of a polyaxial pedicular screw and of an extension piece included in a second embodiment of said equipment.

FIG. 1 represents a polyaxial pedicular screw 1, a rod 2 connecting several of these screws 1, a part 3 connecting this rod 2 to one of these screws 1, a nut 4 enabling assembly of the linking rod 2 to this screw 1 and an extension piece 5 for running down the connecting part 3 and of the nut 4 on the proximal zone of the screw 1.

The screw 1 comprises a proximal threaded stud 6 and a base portion 7. The stud 6 is intended for receiving the part 3 engaged thereon and the nut 4 screwed thereon while the base portion 7 is intended for insertion into the pedicula of a vertebra.

The stud 6 exhibits a threaded cylindrical portion 10, a spherical distal head 11 and a threaded proximal rod 12.

The portion 10 exhibits a zone 15 of reduced diameter, enabling to break its proximal portion after placing and clamping the nut 4, as appears by comparison of FIGS. 2 and 3.

The head 11 exhibits a diameter double that of the portion 10 and looks like a spherical cap. This head 11 is intended for engaging in a proximal cavity 16 delineated by the proximal zone of the base portion 7 and for retention in this cavity 16 by crimping a proximal wall 17 exhibited by this portion 7. After crimping, the wall 17 is shaped in order to have hemispherical proximal form. As shown on FIG. 1, the dimensions of the cavity 16 and of the aperture delineated by the wall 17 after crimping to let through the stud 6 are such that a multidirectional play of this stud 6 with respect to the base portion 7 is possible.

The threaded rod 12 has a diameter smaller than that of the stud 6 and enables the assembly of the extension piece 5 on this stud 6 by screwing. The base portion 7 comprises a proximal collar 18, intended for abutting against the pedicula of the vertebra. This collar 18 exhibits several radial notches 19, notably four notches at 90° to one another, for holding the base portion 7 in rotation when clamping the nut 4.

The linking rod 2 is cylindrical and exhibits such rigidity as to hold several vertebrae with respect to one another. This rod 2 is however deformable in order to be shaped relative to the correction of the rachis to be performed.

The connecting part 3 comprises a rounded section 20 intended for hugging the linking rod 2 and two parallel lateral wings 21.

The distal wing 21 is drilled with a hole for engaging the part 3 on the stud 6 and exhibits a boss 24 delineating a distal cavity 25 substantially hemispherical in shape, coaxial to said hole and of diameter greater than that of the wall 17. There exists therefore a clearance between this wall 17 and the wall of the part 3 delineating the cavity 25, this clearance enabling the angular orientation of the stud 6 with respect to the base portion 7.

The proximal wing 21 comprises a cavity 27 wherein a corresponding conical zone, exhibited by the nut 4, is intended for engaging.

The extension piece 5 comprises an end distal portion 30 and a body 31.

The portion 30 exhibits a tapered bore 32 shaped for screwing the extension piece 5 on the threaded rod 12 and a smooth external wall. The diameter of this portion 30 is smaller than the internal diameter of the thread of the nut 4 so that the nut 4 may run along this portion 30 when engage for sliding on the extension piece 5.

The body 31 is in the form of a metal wire wound into a spiral, with preferably contiguous spires, conferring flexible thereto. This flexible structure facilitates the screwing or the unscrewing of the extension piece 5 when the threaded rod 12 is not parallel to the engaging direction of this extension piece 5.

In practice, the number of screws 1 necessary to the treatment to be performed is placed in the pediculae of the vertebrae affected, then the extension pieces 5 are screwed on the rods 12. The connecting parts 3, with or without the rod(s) 2 engaged in their rounded portions 20, and the nuts 4 are then engaged on these extension pieces 5 and run down along the latter until the parts 3 rest on the walls 17.

After adequate conformation of the rods 2, the nuts 4 are clamped for clamping the connecting parts 3 against the walls 17 and therefore immobilise these parts 3 and the studs 6 with respect to the base portions 7.

After retraction of the extension pieces 5, the studs 6 are cut off at tapered zones 15.

Figure 5:
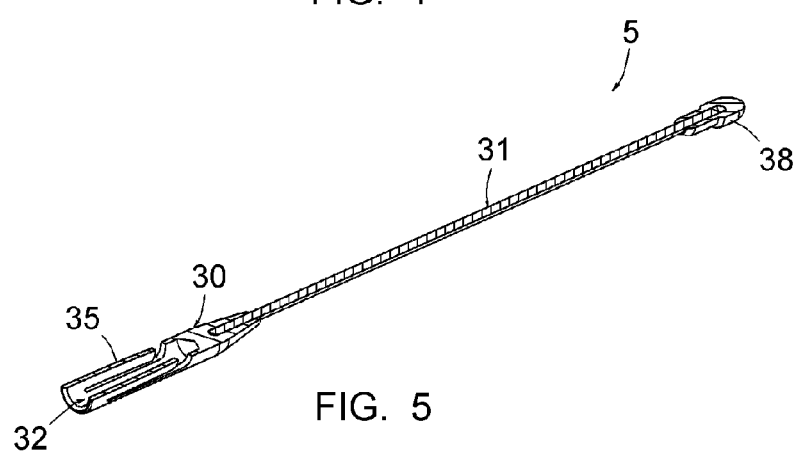
FIG. 5 is a longitudinal cross-sectional view of the extension piece of FIG. 4.
Figure 6:
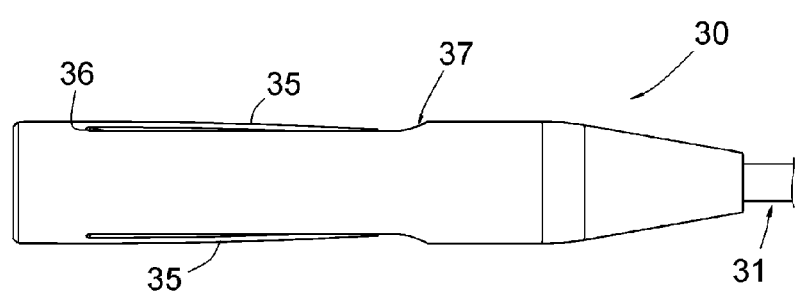
FIG. 6 is an enlarged front view of the distal portion of the extension piece.
Figure 7:
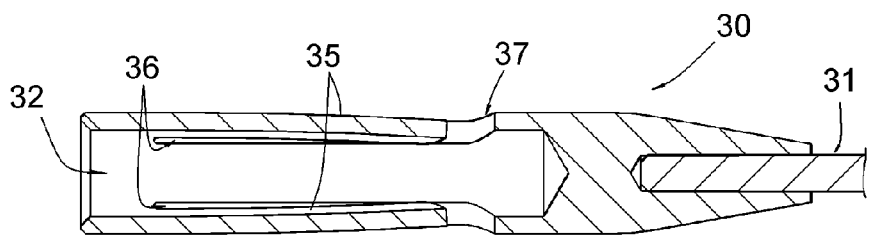
FIG. 7 is a longitudinal cross-sectional view of the distal portion of the extension piece, as seen in FIG. 6.

FIGS. 4 to 7 show another embodiment of the equipment according to the invention, including a polyaxial pedicular screw 1 and an extension piece 5 based on the same concepts than described above. The same references applies to the parts identical or similar to those described above. The linking rod 2 and the connecting part 3 are not shown.

In this case, the stud 6 exhibits an unthreaded proximal rod 12, and the end distal portion 30 has an unthreaded bore 32 and two flexible tabs 35 bent inwardly, which are capable of being elastically bent outwardly by the proximal rod 12 when the latter is inserted in the bore 32. A friction between these tabs 35 and the rod 12 is thus generated, being sufficient for the retention of the extension piece 5 on the stud 6.

In the embodiment shown, the two tabs 35 are diametrically opposed.

These tabs are preferably arranged by U-shaped slots 36 cut through the wall of the end distal portion 30.

Preferably, the bore 32 is narrowing from its distal opened end to its proximal end, until a narrow portion 37 near which are located the proximal ends of the tabs 35.

In the embodiment shown, the body 31 is formed by a single flexible rod, having a tip cap 38 at its proximal end.

As shown by the foregoing, the invention provides a vertebral osteosynthesis equipment enabling to run the nuts 4 down towards the implantation site without retracting the extension pieces 5, this descent showing no risks of losing these nuts 4.

There results that the equipment may be installed more quickly and more reliably.

Obviously, the invention is not limited to the embodiment described above for exemplification purposes but extends to all the embodiments covered by the claims appended therein.

Notably, one would not depart from the framework of the invention by arranging said threaded distal portion 30, so that it enables to screw the nut 4 thereon. This screwing would enable, if necessary, to use the extension piece 5 to bring the part 3 against the base portion 7.

What is claimed is:

1. Vertebral osteosynthesis equipment, including:
   a bone anchoring member comprising a proximal threaded stud and a base portion configured to anchor to a vertebra;
   at least one linking rod;
   a connector having a connector bore configured to engage the proximal threaded stud and the connector further configured to engage the linking rod to thereby connect the linking rod to the bone anchoring member;
   a nut having a threaded nut bore configured to engage the proximal threaded stud to secure the connector to the linking rod and to the proximal threaded stud of the bone anchoring member;
   a retaining member comprising an unthreaded rod extending proximally from the threaded stud;
   an extension member configured to be positioned over the retaining member, the extension member including an unthreaded bore narrowing from an opened distal end toward a proximal end and including flexible, inwardly-bent tabs extending longitudinally in a wall of the extension member, the flexible tabs being configured for elastic outward deformation when the extension member is positioned over the retaining member to generate a holding friction between the flexible tabs and the unthreaded proximal rod of the retaining member, an external dimension of the extension member being sized and configured to be smaller than the connector bore and the nut bore such that the connector and the nut are configured to slide down the extension member toward the proximal threaded stud of the bone anchoring member when the extension member is engaged with the retaining member.

2. Vertebral osteosynthesis equipment according to claim 1 wherein a proximal portion of the extension member is flexible.

3. Vertebral osteosynthesis equipment according to claim 1, wherein the flexible tabs include two diametrically opposed tabs.

4. Vertebral osteosynthesis equipment according to claim 1 wherein the tabs are formed from U-shaped slots cut into the wall of the extension member.

5. Vertebral osteosynthesis equipment according to claim 1 wherein a proximal end of the extension member comprises a single flexible rod with a tip cap at its proximal end.

6. Vertebral osteosynthesis equipment according to claim 1 wherein the bone anchoring member is a pedicular screw.

7. Vertebral osteosynthesis equipment according to claim 1 wherein the bone anchoring member is a lamar hook.

* * * * *